United States Patent [19]

Beversdorf et al.

[11] Patent Number: 4,658,084

[45] Date of Patent: Apr. 14, 1987

[54] HYBRIDIZATION USING CYTOPLASMIC MALE STERILITY AND HERBICIDE TOLERANCE FROM NUCLEAR GENES

[75] Inventors: Wallace D. Beversdorf, Guelph; Lawrence R. Erickson, Mississauga; Ian Grant, Guelph, all of Canada

[73] Assignee: University of Guelph, Guelph, Canada

[21] Appl. No.: 797,917

[22] Filed: Nov. 14, 1985

[51] Int. Cl.[4] .......................... A01H 1/02; A01H 5/00
[52] U.S. Cl. ..................................................... 800/1
[58] Field of Search .......................... 47/58, DIG. 1, 1

[56] References Cited

U.S. PATENT DOCUMENTS

| | | | |
|---|---|---|---|
| 3,842,538 | 10/1974 | Barabas | 47/58 |
| 4,045,912 | 9/1977 | Sun | 47/58 |
| 4,143,486 | 3/1979 | Maan | 47/58 |
| 4,351,130 | 9/1982 | Rutger et al. | 47/58 |
| 4,381,624 | 5/1983 | Lawrence et al. | 47/58 |
| 4,443,971 | 4/1984 | Chaleff | 47/58 |
| 4,517,763 | 5/1985 | Beversdorf et al. | 47/58 |
| 4,535,060 | 8/1985 | Comai | 435/172.3 |
| 4,545,146 | 10/1985 | Davis | 47/58 |

FOREIGN PATENT DOCUMENTS 2139466A 11/1984 United Kingdom .

OTHER PUBLICATIONS

D. E. Falk, K. J. Kasha, and E. Reinbergs, Proceedings of the Fourth International Barley Genetics Symposium, Edinburgh, Jul. 22 to 29, 1981 (Edinburgh University Press) pp. 778 to 785.
Registration of a Shrunken Endosperm, Male-Sterile Germplasm to Facilitate Hybridization in Barley (Reg. No. GP 59), D. E. Falk and K. J. Kasha, Crop Science, vol. 22, Mar.-Apr., 1982, p. 450.
Highlights of Agriculture Research in Ontario, Dec., 1982, at pp. 18-19 in an article by W. D. Beversdorf and David J. Hume entitled "Canola: A New Oilseed Crop for Ontario."
Ontario Ministry of Agriculture and Food Factsheet No. 82-017, Feb., 1982, entitled "Spring Canola in Ontario" by D. J. Hume, R. J. McLaughlin, and W. D. Beversdorf.
I. Bartkowiak-Broda, P. Rousselle, and M. Renard (1979), "Investigation of Two Kinds of Cytoplasmic Male Sterility in Rape (*Brassica napus*, L.)", Genet. Polon. 20:487-497.
Y. Ohkawa, T. Shiga, and T. Ishige (1979), "Male Sterility-Inducing-Cytoplasm in *Brassica campestris* var. *rapifera*,", Annual Report, Division of Genetics, Dept. of Physiol and Genetics, Nat. Inst. of Agric. Sciences, Kannonadi, Yatabe, Tsukuba, Japan, pp. 30-31.
J. D. Palmer, C. R. Shields, D. B. Cohen, and T. J. Orton (1983), "An Unusual Mitochondrial DNA Plasmid in the Genus Brassica", Nature 301:725-728.
P. Rousselle and M. Renard (1982), "Intérêt du Cultivar 'Bronowski' pour l'Obtention de Plantes Male-Steriles Cytoplasmiques chez le Colza (*Brassica napus* L.)," Agronomie 2 (10):951-956.
T. Shiga (1976), "Studies on Heterosis Breeding Using Cytoplasmic Male Sterility in Rapeseed, *Brassica napus* L.," Bull. Nat. Inst. Agric. Sci. Tokyo Series D. 27:75-85.
T. Shiga (1976), "Cytoplasmic Male Sterility and Its Utilization for Heterosis Breeding in Rapeseed, *Brassica napus* L.," JARO 10:177-182.
T. Shiga (1980), "Male Sterility and Cytoplasmic Differentiation," Chapter 12 in Brassica Crops and Wild Allies-Biology and Breeding, Japan Sci. Soc. Press, Tokyo, pp. 205-221.
K. F. Thompson (1972), "Cytoplasmic Male-Sterility in Oil-Seed Rape," Heredity 29(2):253-257.
F. Vedel, C. Mathieu, P. Lebacq, F. Ambard-Bretteville, and R. Remy (1982), "Comparative Macromolecular Analysis of the Cytoplasms of Normal and Cytoplasmic Male Sterile *Brassica napus*," Theor. Appl. Genet. 62:255-262.

(List continued on next page.)

*Primary Examiner*—James R. Feyrer
*Attorney, Agent, or Firm*—Burns, Doane, Swecker & Mathis

[57] ABSTRACT

The process of the present invention provides a convenient route for producing a predetermined hybrid variety of a crop which is capable of undergoing both self-pollination and cross-pollination. Cytoplasmic male sterile plants which also exhibit herbicide tolerance attributable solely to nuclear genes are the key plants for use in the present process. Economical bulk planting of the key plants with either maintainer or restorer plants is made possible. Following cross-pollination from a pollen source which lacks the herbicide tolerance unneeded plants effectively are eliminated by use of a herbicide. For instance, unwanted plants may be effectively eliminated immediately after pollination or prior to pollination in the succeeding generation (provided the requisite genes for herbicide tolerance are present therein) to make possible the existence in an unharmed state of a substantially homogeneous stand of the desired plants. In a preferred embodiment cytoplasmic male sterile plants, plants resulting from the self-pollination of a maintainer, and restorer plants are planted in a substantially random population prior to the application of two different herbicides (as defined) at the appropriate times. The process of the present invention is applicable to grain crops, forage crops, seed-propagated fruits, seed-propagated ornamentals, and industrial species. In a particularly preferred embodiment a predetermined variety of *Brassica napus* (i.e., rape or improved forms thereof known as canola) is formed which is the product of cross-pollination.

70 Claims, No Drawings

OTHER PUBLICATIONS

"Transfer of Cytoplasmically-Inherited Triazene Resistance from Bird's Rape to Cultivated Oilseed Rape (*Brassica campestris* and *B. napus*)," by W. D. Beversdorf, J. Weiss-Lerman, L. R. Erickson, and V. Souza Machado appearing in the Canadian Journal of Genetics and Cytology, vol. XXII, No. 2, Jun. 1980, pp. 167–172.

"Uniparental Inheritance of Chloroplast Atrazine Tolerance in *Brassica Campestris*" by V. Souza Machado, J. E. Bandeen, G. R. Stephenson, and P. Lavigne, Can. J. Plant Sci. 58:977–981, 1978.

Amplification of the *aroA* Gene from *Escherichia coli* Results in Tolerance to the Herbicide Glyphosate", by S. G. Rogers, L. A. Brand, S. B. Holder, E. S. Sharps, and M. J. Brackin, Applied and Environmental Microbiology, 46(1):37–43 (1983).

"Herbicide-Resistant Mutants from Tobacco Cell Cultures", by R. S. Chaleff and T. B. Ray, Science, 223:1147–1150 (1984).

"Selection of Amitrole Tolerant Tobacco Calli and the Expression of This Tolerance in Regenerated Plants and Progeny", by S. R. Singer and C. N. McDaniel, *Theor. Appl. Genet.*, 67:427–432 (1984).

"Selection of Glyphosate-Tolerant Tobacco Calli and the Expression of This Tolerance in Regenerated Plants" by S. R. Singer and C. N. McDaniel, Plant Physiol. 78:411–416 (1985).

"Cloning of Herbicide Resistance Into and Out of Plants", by B. J. Mazur, C. F. Chui, S. C. Falco, R. S. Chaleff and C. J. Mauvais, Biotech '85 USA, Outline Publications, pp. 97–108 (1985).

HYBRIDIZATION USING CYTOPLASMIC MALE STERILITY AND HERBICIDE TOLERANCE FROM NUCLEAR GENES

BACKGROUND OF THE INVENTION

Plant scientists have recognized for many years that the hybridization of closely related plants may result in the production of offspring having a combination of desirable traits which previously were possessed separately by the parent plants. Also, hybrid plants of various crops commonly have possessed a vigor or heterosis which has contributed significantly to the crop yield and accordingly has been of considerable economic importance.

Since the plants selected for hybridization studies commonly are capable of undergoing both self-pollination and cross-pollination, the desired crossing often has been difficult to achieve on a reliable basis while operating on a commercially viable scale. Accordingly, controlled cross-pollination must be achieved in the substantial absence of self-pollination. A common technique heretofore utilized to accomplish this goal has been the use of cytoplasmic male sterile plants as the seed parent which are grown as a substantially uniform population adjacent to another substantially uniform population of plants from which the pollen is derived. Such technique has required precise control of the planting patterns, sufficient pollen transfer from one block of plants to another, and precise control of the seed harvest to preclude comingling of the two different seed products which are produced.

In U.S. Pat. No. 3,842,538 is disclosed a method of hybrid seed grain production wherein the bulk planting of cytoplasmic male sterile parent and the pollen parent is proposed. The seeds capable of forming hybrid plants are thereafter separated from the non-hybrid seeds on the basis of color. Such seed separation technique still would be tedious; however, and is not believed to have been commercially adopted. Articles by D. E. Falk, K. J. Kasha, and E. Reinbergs appearing in *Proceedings of the Fourth International Barley Genetics Symposium,* July 22 to 29, 1981, (Edinburgh University Press), pages 778 to 785, and by D. E. Falk and K. J. Kasha appearing in *Crop Science,* Vol. 22, March-April, 1982, page 450, discuss a tight linkage between genetic male sterility and a shrunken endosperm. See also, U.S. Pat. No. 4,351,130 which discloses a process for cereal production wherein tall male parents and short female parents can be grown in the same planting area, and after pollination the male parents are destroyed.

While considerable success has been realized in the past through the adoption of various well-known hybridization techniques, the need nevertheless has remained for alternate, less tedious, more efficient, or otherwise improved hybridization routes. Additionally, for many crops commercially feasible hybridization technology is yet to be implemented in spite of continuing research by dedicated plant scientists working around the world.

An example of a crop which is yet to benefit from the commercial availability of seed capable of growing hybrid plants is rape (i.e., *Brassica napus* or *Brassica campestris*). While not necessarily recognized by the general public, rape (and particularly high-quality forms thereof known as canola) is being grown as an increasingly important oilseed crop and a source of rape-seed meal in many parts of the world. The oil may serve as a high-quality vegetable oil and the meal may be used as a nutritious protein concentrate for livestock. The importance of rape as an agronomic crop is discussed in (1) *Highlights of Agricultural Research in Ontario,* December 1982, at pages 18-19 in an article by W. D. Beversdorf and David J. Hume, entitled "Canola: A New Oilseed Crop for Ontario," and in (2) The Ontario Ministry of Agriculture and Food Factsheet No. 82-017, February 1982, entitled, "Spring Canola in Ontario" by D. J. Hume, R. J. McLaughlin and W. D. Beversdorf.

Representative publications of researchers working in the area of rapeseed technology who have identified cytoplasmic male sterility in rape plants are identified below:

Bannerot, H., Boulidard, I., Cauderon, Y., and Tempe, J., "Cytoplasmic Male Sterility Transfer From Raphanus to Brassica," *Proc. Eucarpia Meeting Cruciferae Vegetable Crop,* Sect. 25:52-54 (1974).

Bartkowiak-Broda, I., Rousselle, P., and Renard, M., "Investigation of Two Kinds of Cytoplasmic Male Sterility in Rape (*Brassica napus* L.)," *Genet. Polon.* 20:487-497 (1979).

Ohkawa, Y., Shiga, T., and Ishige, T., "Male Sterility-Inducing-Cytoplasm in *Brassica campestris* var. *rapifera, Annual Report,* Division of Genetics, Dept. of Physiol. and Genetics, Nat. Inst. of Agric. Sciences, Kannondai, Yatabe, Tsukuba, Japan, pp. 30-31 (1979).

Palmer, J. D., Shields, C. R., Cohen, D. B., and Orton, T. J., "An Unusual Mitochondrial DNA Plasmid in the Genus Brassica," *Nature* 301:725-728 (1983).

Rousselle, P., and Renard, M., "Interet du cultivar <<Bronowski>> pour l'obtention de plantes male-steriles cytoplasmiques chez le colza (*Brassica napus* L.)," *Agronomie* 2 (10):951-956 (1982).

Shiga, T., "Studies on Heterosis Breeding Using Cytoplasmic Male Sterility in Rapeseed., *Brassica napus* L.", *Bull. Nat. Inst. Agric. Sci.,* Tokyo Series D. 27:75-85 (1976).

Shiga, T., "Cytoplasmic Male Sterility and Its Utilization for Heterosis Breeding in Rapeseed (*Brassica napus* L.)", *JARQ* 10:177-182 (1976).

Shiga, T., "Male Sterility and Cytoplasmic Differentiation," Chapter 12 in *Brassica Crops and Wild Allies-Biology and Breeding,* Japan Sci. Soc. Press, Tokyo, pp. 205-221 (1980).

Thompson, K. F., "Cytoplasmic Male-Sterility in Oil-Seed Rape," *Heredity* 29(2):253-257 (1972).

Vedel, F., Mathieu, C., Lebacq, P., Ambard-Bretteville, F., and Remy, R., "Comparative Macromolecular Analysis of the Cytoplasms of Normal and Cytoplasmic Male Sterile *Brassica napus,*" *Theor. Appl. Genet.* 62:255-262 (1982).

It has also been recognized in the past that weed control is an important consideration for those who choose to grow rape. Unchecked weeds will lessen the ultimate yield and can significantly reduce the quality by unavoidable contamination from diverse seeds which are harvested along with the desired crop. In order to deal with the weed problem various herbicide tolerant varieties of rape have been proposed so that unwanted weeds can be efficiently eliminated while growing in close proximity to the rape plants. See in this regard, "Transfer of Cytoplasmically-Inherited Triazine Resistance From Bird's Rape to Cultivated Oilseed Rape (*Brassica campestris* and *B. napus*)," by W. D. Beversdorf, J. Weiss-Lerman, L. R. Erickson and V.

Souza Machado appearing in the *Canadian Journal of Genetics and Cytology*, Volume XXII, No. 2, June 1980, pages 167–172. See also "Uniparental Inheritance of Chloroplast Atrazine Tolerance in Brassica Campestris" by V. Souza Machado, J. D. Bandeen, G. R. Stephenson and P. Lavigne, *Can. J. Plant Sci.*, 58:977–981, 1978.

In our U.S. Pat. No. 4,517,763 entitled, "Hybridization Process Utilizing a Combination of Cytoplasmic Male Sterility and Herbicide Tolerance" is disclosed a hybridization process in which the bulk planting of the parents is made possible. This disclosure additionally was published as U.K. Patent Application GB No. 2,139,466A on Nov. 14, 1984.

It additionally has been recognized that plants can be identified by plant scientists which exhibit herbicide tolerance which is attributable soley to nuclear genes. See, for instance the following representative publications in this area:

Rogers, S. G., Braud, L. A., Holder, S. B., Sharps, E. S. and Brackin, M. J., "Amplification of the aroA Gene from Escherichia Coli Results in Tolerance to Herbicide Glyphosate", *Applied and Environmental Microbiology*, 46 (1):37–43 (1983).

Chaleff, R. S. and Ray, T. B., "Herbicide-Resistant Mutants from Tobacco Cell Cultures", *Science*, 223:1147–1150 (1984).

Singer, S. R. and McDaniel, C. N., "Selection of Amitrole Tolerant Tobacco Calli and the Expression of this Tolerance in Regenerated Plants and Progeny", *Theor. Appl. Genet.*, 67:427–432 (1984).

Singer, S. R. and McDaniel, C. N., "Selection of Glyphosate-Tolerant Tobacco Calli and the Expression of this Tolerance in Regenerated Plants", *Plant Physiol.* 78:411–416 (1985).

Comai, L., U.S. Pat. No. 4,535,060, "Inhibition Resistant 5-Enolpyruvyl-3-Phosphoshickimate Synthetase, Production and Use" (1985).

See also our copending U.S. Ser. No. 797,916, filed concurrently herewith, entitled, "Hybridization Process Utilizing a Combination of Cytoplasmic Male Sterility, Cytoplasmic Herbicide Tolerance, and Herbicide Tolerance Attributable Solely to Nuclear Genes".

It is an object of the present invention to provide an improved hybridization process for use in forming a predetermined hybrid variety of a crop which is capable of undergoing both self-pollination and cross-pollination.

It is an object of the present invention to provide an improved hybridization process for use in forming a predetermined hybrid variety of a crop which is capable of undergoing both self-pollination and cross-pollination wherein the seed parent is cytoplasmic male sterile and wherein the pollen parent conveniently may be grown in bulk with the seed parent during a step of the process without the need for a precise planting pattern and the disadvantages associated therewith.

It is an object of the present invention to provide an improved hybridization process for use in forming a predetermined hybrid variety of a crop wherein the cross-fertilization of cytoplasmic male sterile plants with maintainer plants readily may be accomplished.

It is an object of the present invention to provide an improved hybridization process for use in forming a predetermined hybrid variety of a crop which is capable of undergoing both self-pollination and cross-pollination wherein the desired product may be formed on a reliable basis.

It is an object of the present invention to provide an improved hybridization process for use in forming a predetermined hybrid variety of a crop which is capable of undergoing both self-pollination and cross-pollination which is suitable for utilization on an economical basis on a commercially attractive scale.

It is an object of the present invention to provide an improved hybridization process for use in forming a predetermined hybrid variety of a crop which is capable of undergoing both self-pollination and cross-pollination wherein the desired product in a preferred embodiment additionally exhibits herbicide tolerance which makes possible the selective destruction with ease of troublesome weeds growing within the hybrid crop area.

It is an object of the present invention to provide an improved hybridization process which particularly is suited for use when forming a predetermined hybrid variety of rape (e.g., *Brassica napus*), and to thereby provide a commercially practicable route for forming hybrid rape.

It is another object of the present invention to provide a new and useful *Brassica napus* seed product which is suitable for use when carrying out the process of the present invention.

It is a further object of the present invention to provide a *Brassica napus* seed product which is capable of forming $F_1$ hybrid rape plants which exhibit tolerance to at least one herbicide attributable solely to nuclear genes.

These and other objects and advantages will be apparent to those skilled in the art from reading of the following description and appended claims.

SUMMARY OF THE INVENTION

It has been found that an improved process for producing a substantially homogenous population of plants of a predetermined hybrid variety of a crop which is capable of undergoing both self-pollination and cross-pollination comprises:

(a) growing in a first planting area a substantially random population of (1) cytoplasmic male sterile plants which exhibit tolerance to at least one herbicide attributable solely to homozygous dominant nuclear genes, and (2) male fertile plants which are capable of pollinating the cytoplasmic male sterile plants and which lack the herbicide tolerance because the presence of homozygous recessive nuclear genes for such trait, whereby the cytoplasmic male sterile plants (1) and the male fertile plants (2) are pollinated with pollen derived from the male fertile plants and seed is formed on the cytoplasmic male sterile plants and on the male fertile plants, (b) harvesting in bulk the seed which is formed on the plants of the first planting area, (c) growing at least a portion of the seed from step (b) in a second planting area in the absence of segregation between the seed derived from the cytoplasmic male sterile plants which exhibit the herbicide tolerance attributable solely to homozygous dominant nuclear genes and the male fertile plants which lack the herbicide tolerance because of the presence of homozygous recessive nuclear genes for such trait, and (d) contacting prior to pollination substantially all of the plants present in the second planting area with a herbicide which is effective to destroy the plants resulting from seed formed on the male fertile plants of the first planting area, whereby a substantially homogeneous population of a predetermined hybrid variety is formed which resulted from seed formed on the male sterile plants of the first planting area.

It has been found that an improved process for producing seed capable of forming a predetermined hybrid variety of a crop which is capable of undergoing both self-pollination and cross-pollination comprises:

(a) growing in a planting area a substantially random population of (1) cytoplasmic male sterile plants which exhibit tolerance to at least one herbicide attributable solely to nuclear genes, and (2) male fertile plants which are capable of pollinating the cytoplasmic male sterile plants and which lack the herbicide tolerance because of the absence of the required nuclear genes for such trait, whereby the cytoplasmic male sterile plants (1) are pollinated with pollen derived from the male fertile plants (2), (b) contacting following the pollination substantially all of the plants present in the planting area with a herbicide which is effective to destroy the male fertile plants and which is ineffective to destroy the cytoplasmic male sterile plants because of the herbicide tolerance attributable solely to the nuclear genes, and (c) harvesting seed from the cytoplasmic male sterile plants which is capable of forming the hybrid plants in the substantial absence of seed from the male fertile plants which initially grew in the planting area.

It has been found that an improved process for producing a substantially homogeneous population of plants of a predetermined hybrid variety of a crop which is capable of undergoing both self-pollination and cross-pollination comprises:

(a) growing in a first planting area a substantially random population of (1) cytoplasmic male sterile plants which exhibit tolerance to a first at least one herbicide which is attributable solely to homozygous nuclear genes and exhibit tolerance to a second at least one herbicide which is attributable solely to different homozygous nuclear genes, and (2) male fertile plants which are homozygous recessive maintainer plants for the cytoplasmic male sterile plants and which lack the herbicide tolerance to the first at least one herbicide because of the absence of the required nuclear genes of such trait and exhibit tolerance to the second at least one herbicide attributable solely to the homozygous nuclear genes, whereby the cytoplasmic male sterile plants (1) and the maintainer plants are pollinated with pollen derived from the maintainer plants and seed is formed on the cytoplasmic male sterile plants and on the maintainer plants, (b) harvesting in bulk the seed which is formed on the plants of the first planting area, (c) growing in a second planting area a substantially random population of plants derived from seed harvested in step (b) together with homozygous dominant fertility restorer plants for the cytoplasmic male sterile plants which exhibit herbicide tolerance to the first at least one herbicide attributable solely to the homozygous nuclear genes and lack tolerance to the second at least one herbicide because of the absence of the required nuclear genes for such trait, (d) contacting prior to pollination substantially all of the plants present in the second planting area with the first herbicide which is effective to destroy the plants resulting from seed formed on the maintainer plants in step (a) whereby cytoplasmic male sterile plants and restorer plants remain, (e) pollinating the cytoplasmic male sterile plants and the restorer plants of step (d) with pollen derived from the restorer plants and seed is formed on the cytoplasmic male sterile plants and on the restorer plants, (f) harvesting in bulk the seed which is formed on the plants remaining in the second planting area, (g) growing in a third planting area a substantially random population of plants derived from seed harvested in step (f), and (h) contacting substantially all of the plants present in the third planting area with the second herbicide which is effective to destroy the plants resulting from the seed formed on the restorer plants of step (e), whereby a substantially homogeneous population of male fertile $F_1$ hybrid plants of a predetermined variety is formed.

It has been found that an improved process for producing a seed capable of forming a predetermined hybrid variety of a crop which is capable of undergoing both self-pollination and cross-pollination comprises:

(a) growing in a first planting area a substantially random population of (1) cytoplasmic male sterile plants which exhibit tolerance to a first at least one herbicide which is attributable solely to homozygous nuclear genes and exhibit tolerance to a second at least one herbicide which is attributable solely to different homozygous nuclear genes, and (2) male fertile plants which are homozygous recessive maintainer plants for the cytoplasmic male sterile plants and which lack the herbicide tolerance to the first at least one herbicide because of the absence of the required nuclear genes for such trait and exhibit tolerance to the second at least one herbicide attributable solely to the homozygous nuclear genes, whereby the cytoplasmic male sterile plants (1) and the maintainer plants are pollinated with pollen derived from the maintainer plants and seed is formed on the cytoplasmic male sterile plants and on the maintainer plants, (b) harvesting in bulk the seed which is formed on the plants of the first planting area, (c) growing in a second planting area a substantially random population of plants derived from seed harvested in step (b) together with homozygous dominant fertility restorer plants for the cytoplasmic male sterile plants which exhibit herbicide tolerance to the first at least one herbicide attributable solely to homozygous nuclear genes and lack tolerance to the second at least one herbicide because of the absence of the required nuclear genes for such trait, (d) contacting prior to pollination substantially all of the plants present in the second planting area with the first herbicide which is effective to destroy the plants resulting from seed formed on the maintainer plants in step (a) whereby cytoplasmic male sterile plants and restorer plants remain, (e) pollinating said cytoplasmic male sterile plants and the restorer plants of step (d) with pollen derived from the restorer plants, (f) subsequently contacting substantially all of the remaining plants present in the second planting area with the second herbicide which is effective to destroy the restorer plants and which is ineffective to destroy cytoplasmic male sterile plants because of the herbicide tolerance attributable solely to the homozygous nuclear genes, and (g) harvesting seed from the cytoplasmic male sterile plants which is capable of forming $F_1$ hybrid plants in the substantial absence of seed from the maintainer and restorer plants which initially grew in the second planting area.

A *Brassica napus* seed product is provided consisting of a substantially homogeneous assemblage of seeds which upon growth yield rape plants which exhibit a combination of cytoplasmic male sterility and tolerance to at least one herbicide attributable solely to homozygous dominant nuclear genes.

A *Brassica napus* seed product is provided consisting of a substantially homogeneous assemblage of seeds which upon growth yield rape plants which exhibit a combination of cytoplasmic male sterility and tolerance to at least one herbicide attributable solely to homozygous recessive nucelar genes.

A *Brassica napus* seed product is provided consisting of a substantially homogeneous binary admixture of seeds which upon growth yields:
(1) a first rape plant component which exhibits cytoplasmic male sterility and tolerance to at least one herbicide which is attributable solely to homozygous dominant nuclear genes, and
(2) a second rape plant component which is capable of pollinating the first rape plant component, is a homozygous recessive maintainer for the cytoplasmic male sterility of the first rape plant component, and which lacks the herbicide tolerance because of the presence of homozygous recessive nuclear genes for such trait.

A *Brassica napus* seed product is provided consisting of a substantially homogenous binary admixture of seeds which upon growth yields:
(1) a first rape plant component which exhibits cytoplasmic male sterility and tolerance to at least one herbicide which is attributable solely to homozygous dominant nuclear genes, and
(2) a second rape plant component which is capable of pollinating the first rape plant component, is a homozygous recessive maintainer for the cytoplasmic male sterility of the first rape plant component, and which lacks the herbicide tolerance because of the presence of homozygous recessive nuclear genes for such trait.

A *Brassica napus* seed product is provided consisting of a substantially homogeneous binary admixture of seeds which upon growth yields:
(1) a first rape plant component which exhibits cytoplasmic male sterility and tolerance to at least one herbicide which is attributable solely to homozygous recessive nuclear genes, and
(2) a second rape plant component which is capable of pollinating the first rape plant component, is a homozygous dominant fertility restorer for the first rape plant component, and which lacks the herbicide tolerance because of the presence of homozygous dominant nuclear genes for such trait.

A *Brassica napus* seed product consisting of a substantially homogeneous binary admixture of seeds which upon growth yields:
(1) a first rape plant component which exhibits cytoplasmic male sterility and tolerance to at least one herbicide which is attributable solely to homozygous recessive nuclear genes, and
(2) a second rape plant component which is capable of pollinating the first rape plant component, is a homozygous dominant fertility restorer for the first rape plant component, and which lacks the herbicide tolerance because of the presence of homozygous dominant nuclear genes for such trait.

A *Brassica napus* seed product is provided consisting of a substantially homogeneous assemblage of seeds which upon growth yields male fertile $F_1$ hybrid rape plants which possess tolerance to at least one herbicide attributable solely to nuclear genes.

DESCRIPTION OF THE PREFERRED EMBODIMENTS

The hybridization concept of the present invention is deemed to be generally applicable for the formation of a predetermined variety of any crop which is capable of undergoing both self-pollination and cross-pollination. For the purposes of the present invention hybridization is deemed to occur when two parent plants which are not identical from the nuclear and cytoplasmic point of view are cross-pollinated. Accordingly, seed capable of forming a hybrid plant is deemed to result from the fertilization of a cytoplasmic male sterile plant with pollen from either a maintainer or a restorer plant which is capable of pollinating the same. A predetermined hybrid variety of a grain crop, a forage crop, a seed-propagated fruit, a seed-propagated ornamental, or of an industrial species, etc., may be formed in accordance with the process of the present invention. For the purposes of the present invention grain crops are those which are grown primarily for seed, and forage crops are those which are grown primarily for the consumption of plant parts other than seed such as the foliage or other vegetative structure.

Representative grain crops which may be hybridized in accordance with the process of the present invention include cereals (e.g., wheat, oats, barley, rye, corn, triticale, sorghum, etc.), grain legumes (e.g., field beans, peas, peanuts, lentils), and oilseeds (e.g., flax, mustard, safflower, sunflower, soybeans, rape, etc.). Representative forage crops which may be hybridized in accordance with the process of the present invention include alfalfa, sugar beets, onions, peppers, seed propagated potatoes, turnips, cabbage, broccoli, brome grass, etc. Representative seed-propagaged fruits which may be hybridized in accordance with the process of the present invention include tomatoes, peppers, watermelons, etc. Representative seed-propagated ornamentals which may be hybridized in accordance with the process of the present invention include petunias, marigolds, etc. Representative industrial species which may be hybridized in accordance with the process of the present invention include poplar trees, maple trees, cotton, fibre flax, tobacco, kelp, etc.

The process of the present invention is particularly suited for the formation of a hybrid variety of a crop of the family Brassicaceae, which is sometimes designated the Cruciferae family or the Mustard family. Within this family one may select with greater particularity a crop of the genus Brassica (e.g., a hybrid variety of rape plant classified as *Brassica napus* or *Brassica campestris*). Each of these previously named species occurs in a spring and winter (fall-seed) type. High-quality forms of rapeseed which are used primarily as a source of vegetable oil and of rapeseed meal (a protein concentration for livestock) are commonly referred to as canola. For instance, canola often identifies quality rapeseed which is low in erucic acid (less than 5%) and glucosinolates (less than 3 milligrams per gram of oil-free meal). Alternatively, rapeseed may be employed in the production of lubricants, paints, varnishes, and plastics in accordance with known technology.

When carrying out the process of the present invention, it is necessary to select female parent plants which exhibit a combination of cytoplasmic male sterility and herbicide tolerance which is attributable solely to nuclear genes. For the purposes of the present invention a plant is considered to be male sterile when it is incapable of dehiscing functional pollen (e.g., is incapable of in situ fertilization of an egg). In all instances the male sterility must be manifest because of the specific type of cytoplasm which is present. It further commonly is essential when forming grain crops that the cytoplasmic male sterile plants possess the ability to form seed which yields fully fertile hybrid plants following pollination from a pollen source which possesses homozygous dominant fertility restoring genes which are capable of interacting with the cytoplasm. The cytoplasmic male sterile plants will possess the ability to form seeds which yield cytoplasmic male sterile plants following pollination from a pollen source which lacks the dominant fertility-restoring genes.

For the purposes of the present invention a plant is considered to possess herbicide tolerance when it has the ability to withstand or to endure a given herbicide while carrying on its normal plant functions. In all instances the herbicide tolerance relied upon during the practice of the present invention must be attributable solely to nuclear genes. In contrast, plants which lack such herbicide tolerance are significantly impaired or otherwise destroyed under the same conditions. Such lack of herbicide tolerance also can be manifest through the prevention of seed germination whereby the potential plant is destroyed at a very early stage in its development. In a preferred embodiment the herbicide tolerance is attributable solely to homozygous dominant nuclear genes. In another embodiment in which unwanted parent plants are destroyed immediately following pollination and it is not essential that the resulting hybrid variety also exhibit such herbicide tolerance, the herbicide tolerance is attributable solely to heterozygous dominant nuclear genes. In a further embodiment the herbicide tolerance is attributable solely to homozygous recessive nuclear genes for such trait. In most instances the herbicide tolerance is imparted by a single pair of genes; however, herbicide tolerance attributable solely to more than one gene pair likewise may be utilized.

The mode of operation of the particular herbicide employed in the process of the present invention can be varied widely so long as the required elimination of unwanted plants can be selectively accomplished without undue damage to the herbicide tolerant plants at the appropriate stage in the process. A herbicide should be employed which is recognized to be safe for agricultural use. The herbicide employed when carrying out the process of the present invention may be selected from a wide variety of herbicide classes so long as it is used in conjunction with plants which possess the nuclear genes required to impart the necessary herbicide tolerance. Representative compounds from which the herbicide may be selected are as follows: aliphatic carboxylics (e.g., trichloroacetic acid, dalapon, etc.), amides and acid amides (e.g., alachlor, metolachlor, etc.), benzoics (e.g., dicamba, chloramben, etc.), bipyridyliums (e.g., paraquat, diquat, etc.), carbamates (e.g.. barban, desmedipham, etc.), cyclohexenones (e.g., sethoxydim, etc.), dinitroanilines (e.g., trifluralin, oryzalin etc.), diphenylethers (e.g., acifluorfen, nitrofen, etc.), glycine derivatives (e.g., glyphosate sometimes identified as phosphonomethyl glycine, etc.), imidazolinones (e.g., imazaquine, etc.), nitriles (e.g., bromoxynil, ioxynil, etc.) phenols (e.g., dinofeb, etc.), phenoxycarboxylics (e.g., 2,4-D, MCPA, etc.) phenoxy-phenoxy and related compounds (e.g., diclofop, fluazifop), pyridines (e.g., picloram, clopyralid, etc.), pyrimidines (e.g., bromicil, terbicil, etc.), sulfonylureas (e.g., chlorsulfuron, sulfometuron methyl, etc.), thiocarbamates (e.g., EPTC, butylate, etc.), triazines (e.g. atrazine, simazine, metribuzin, etc.), ureas (e.g., diuron, linuron, etc.), amitrole, and bentazon.

Preferred herbicides are the sulfonylureas, glycine derivatives, and imidazolinones. In a particularly preferred embodiment the herbicide selected is chlorosulfuron which is believed to function by the inhibition of amino acid metabolism. Such herbicide is commercially available from DuPont Chemical Company under the GLEAN trademark. In a further particularly preferred embodiment the herbicide is glyphosate (phosphonomethyl glycine). Such herbicide is available commercially from Monsanto Corporation under the ROUNDUP trademark. Also, amitrole and bentazon may be used to advantage as herbicides in the present process.

The herbicide can be applied by conventional means prior to pollination or after pollination. Prior to pollination the herbicide may be applied to seeds at the pre-emergence stage so as to prevent germination or to the young seedling plants at the post-emergence stage following germination (i.e., at a preanthesis stage). Alternatively, the herbicide may be applied to older plants. The herbicide may be applied to the entire plant or to plant parts, such as to the roots through the soil, to the leaves, to the stems, etc. In most instances it is recommended that the herbicide be applied by spraying the foliage at rate specified by its manufacturer. However, the optimum application rate for a given herbicide can be determined by routine experimentation.

The key cytoplasmic male sterile female parent plants for use in the process of the present invention can be derived by any one of number of routes available to plant scientists. Commonly, male fertile plants having the requisite herbicide tolerance attributable solely to nuclear genes are isolated, and such herbicide tolerance is next transferred to plants which possess the required cytoplasm to impart male sterility. For instance, large populations of plants can be subjected to a given herbicide to select for plants which through a spontaneous genetic variation will possess the nuclear genes required to impart herbicide tolerance. Alternatively, the required herbicide tolerance can be developed through in vitro selection from a tissue culture medium which includes the herbicide intended for use in the process. Such in vitro selection may be carried out using known technqiues at the protoplast level, the suspension culture level, the callus culture level, the micropore culture level, etc. Mutagens optionally can be employed to further encourage genetic variation within the plants being evaluated. Alternatively, once the required genes are identified they can be transferred to the female parent through the application of genetic engineering techniques. See, for instance, "Cloning of Herbicide Resistance Into and Out of Plants" by B. J. Mazur, C. F. Chui, S. C. Falco, R. S. Chaleff and C. J. Mauvais, Biotech '85 USA, Online Publications, pp. 97–108 (1985), which is herein incorporated by reference. In all instances the nuclear source of the herbicide tolerance can be confirmed by observing the mode of transmission of the tolerance in subsequent generations. The agronomic character of herbicide tolerant plants commonly will be improved by hybridization and selection using standard plant breeding techniques.

Maintainer plants which are capable of pollinating the plants which exhibit cytoplasmic male sterility must, by necessity, be homozygous maintainers with respect to recessive fertility restorer genes which interact with the requisite cytoplasm. They also must lack herbicide tolerance with respect to the same herbicide which can be tolerated by cytoplasmic male sterile plants which is attributable solely to nuclear genes. Suitable maintainer plants can be developed simultaneously with the search for the cytoplasmic male sterile plants since they commonly are necessary in order to easily confirm whether the desired cytoplasm is in fact present. The maintainer plants selected commonly possess substantially the same nuclear genotype as the cytoplasmic male sterile plants with the exception that the maintainer plants lack the required nuclear genes for herbicide tolerance when grown in a bulk planting area. Controlled introgression of the recessive genes for fertility restoration from partial male steriles into fertile cytoplasms may be accomplished. Such partial male steriles are heterozygous since only one half of the gametes produced are recessive for the fertility restoration gene. Male parents which have been found to induce cytoplasmic male sterility following wide hybridization may be tested for the presence of recessive genes for fertility restoration. Also, naturally recurring populations or currently grown cultivars may be evaluated by know techniques for the presence of recessive genes for fertility restoration. The agronomic properties of the key plants may be improved through well known plant breeding techniques. The progeny of a cross between the cytoplasmic male sterile plants and the maintainer plants are always cytoplasmic male sterile and may or may not exhibit herbicide tolerance, depending on whether such tolerance is attributable to dominant or recessive nuclear genes for such trait. Once a maintainer plant is located it must be multiplied by self-pollination, or optionally by clonal propagation. As will be apparent to those skilled in plant breeding, there are several different cytoplasmic male sterile systems available in *Brassica napus*, and a given rape cultivar can be a maintainer or a restorer depending upon the system which is selected. Maintainer plants for the POL and OGU cytoplasmic systems are found in virtually all *Brassica napus* cultivars and accordingly are simple to identify by test-crossing. Maintainer plants for the NAP cytoplasmic system have been isolated in the Bronowski and Isuzunatane cultivars of *Brassica napus*. Maintainer plants for the CTR cytoplasmic system have been isolated in the Bronowski cultivar of *Brassica napus*.

Restorer plants are capable of pollinating the female parent plants which exhibit cytoplasmic male sterility and herbicide tolerance which is attributable solely to nuclear genes. The restorer plants are readily available and require little investigation in order to locate. These plants must, by necessity, be homozygous restorers with respect to the dominant fertility restorer genes which interact with the requisite cytoplasm. Because of the dominant transmission mode these plants often are far more common than the maintainer plants in a given plant population. Such restorer plants when grown in a bulk planting area lack herbicide tolerance which is attributable solely to nuclear genes with respect to the same herbicide as the cytoplasmic male sterile plants. Restorer plants for the POL and OGU cytoplasmic systems can be the Italy cultivar of *Brassica napus*, and the Zem cultivar of *Brassica juncea*. In the NAP and CTR cytoplasmic systems virtually all *Brassica napus* cultivars are restorers and may be readily located by simple test crosses.

The process of the present invention offers the advantage of simple bulk planting of (1) cytoplasmic male sterile plants which exhibit tolerance to at least one herbicide attributable solely to nuclear genes and (2) male fertile plants which are capable of pollinating the same and which lack the herbicide tolerance because of the absence of the required nuclear genes for such trait. The male fertile plants may be either maintainer plants or restorer plants as previously discussed. Conventional planting techniques may be employed while forming a random mixture of the two plants. There is no requirement that equal quantities of the two seed types be employed. For instance, the seeds capable of forming the cytoplasmic male sterile and herbicide tolerant plants which serve as the seed parent commonly will be provided in the major amount. Accordingly, such seed will commonly comprise 60 to 90 percent or more of the total amount of seed planted (i.e., the seed which produces the male and female parents). Accordingly, one male fertile plant can commonly pollinate more than one male sterile female parent plant. As will be apparent to those skilled in seed production technology, the relative proportions of the two parent plant types should be adjusted so as to achieve the desired level of pollination on a consistent basis while utilizing the minimum quantity of male fertile male parent plants.

When carrying out the process of the present invention, respective parent plants which have overlapping flowering cycles should be selected. Additionally, the process of the present invention relies upon conventional modes of pollen transfer (e.g., pollen-carrying insects such as bees and/or the wind). Also, conventional techniques for harvesting the subject crop may be employed.

In a preferred embodiment of the process, following bulk planting in a first planting area of (1) cytoplasmic male sterile plants which exhibit tolerance to at least one herbicide attributable solely to homozygous dominant nuclear genes, and (2) male fertile plants which are capable of pollinating said cytoplasmic male sterile plants and which lack the herbicide tolerance because of the presence of homozygous recessive nuclear genes for such trait, the resulting plants may be grown to maturity and the resulting seed formed on each of the plant components harvested in bulk. At least a portion of the seed produced thereby may next be planted in a second planting area without segregation to yield new plants to which a herbicide is applied prior to pollination to yield a substantially uniform population of a predetermined hybrid variety which results from seed formed on the male sterile plants of the first planting area. If the male fertile plant component present in the first planting area was a restorer, seed formed on the plants in the second area may simply be harvested, and the herbicide conveniently applied by the farmer in conjunction with a weed control program. However, in the embodiment wherein the male plant component of the first planting area was a maintainer, one conveniently may grow in pollinating proximity to the plants remaining in the second planting area following herbicide application a substantially homogeneous population of restorer plants for the male fertility. The respective substantially homogeneous populations conveniently may take the form of alternating rows, strips, or blocks which are amenable to selective harvesting. Seed capable of forming a predetermined male fertile $F_1$ hybrid variety may then be selectively recovered from the cytoplasmic male sterile plants of the second planting area. Such restorer plants which are grown near the second planting area may or may not possess herbicide tolerance.

In a further preferred embodiment of the process wherein the herbicide is applied at the post-flowering stage to a two-component mixture of randomly grown plants which include a maintainer and the resulting seed is harvested, the resulting seed may next be planted in pollinating proximity to restorer plants which pollinate the cytoplasmic male sterile plants Such pollinating proximity may take the form of bulk planting of adjoining substantially homogeneous plant populations. If bulk planting with restorer plants is employed, the restorer plants may be eliminated by the herbicide following pollination and the selective harvest from the remaining cytoplasmic male sterile plants of seed capable of forming $F_1$ hybrid plants is made possible.

In a particularly preferred embodiment the maintainer and restorer plants are each tolerant to different herbicides wherein such tolerances are attributable solely to different homozygous nuclear genes (i.e., homozygous dominant genes or homozygous recessive genes) and the cytoplasmic male sterile plants are tolerant to both of the herbicides. Following pollination of the cytoplasmic male sterile plants with pollen derived from the maintainer plants in a random first planting area, the seed may be harvested and planted in random in a second planting area together with seed capable of forming the restorer plants. Prior to pollination in the second planting area plants resulting from the seed derived from the self-pollinated maintainer are destroyed through the application of a herbicide. Next the restorer plants are destroyed following pollination or in the next generation in a third planting area through the application of a different herbicide. For instance, the self-pollinated maintainer plants could be destroyed through the application of chorsulfuron or glyphosate and the restorer plants destroyed through the application of the other herbicide. The resulting $F_1$ hybrid is tolerant to same herbicides provided the required genes for such tolerance are present therein.

In a further particularly preferred embodiment the cytoplasmic male sterile plants are maintained in a preliminary planting area wherein substantially uniform populations of the two parents are grown in pollinating proximity for one or more generations prior to obtaining the seed which forms the cytoplasmic male sterile plants in the first planting area. In such embodiment the maintainer plants which are grown in the preliminary planting area possess the same herbicide tolerance as the cytoplasmic male sterile plants which is attributable solely to the same homozygous nuclear genes. Accordingly, in this manner the cytoplasmic male sterile plants can be maintained for a number of generations without unwanted segregation with respect to the herbicide tolerance required at a later stage of the process.

The present invention provides for the first time the ability to form a *Brassica napus* seed product consisting of a substantially homogeneous assemblage of seeds which upon growth yield rape plants which exhibit a combination of cytoplasmic male sterility and herbicide tolerance attributable solely to homozygous nuclear genes (i.e., either homozygous dominant or homozygous recessive genes). Also *Brassica napus* binary admixtures of such seeds with seeds which form either maintainer or restorer plants having the appropriate herbicide tolerance to carry out the present process are provided. Additionally, the formation of a substantially homogeneous assemblage of *Brassica napus* seeds is made possible which upon growth yield male fertile $F_1$ hybrid rape plants which possess herbicide tolerance to at least one herbicide attributable solely to nuclear factors Accordingly, the farmer may conveniently eliminate weeds with an appropriate herbicide when the hybrid crop is grown.

Although the invention has been described with preferred embodiments, it is to be understood that variations and modifications may be resorted to as will be apparent to those skilled in the art. Such variations and modifications are to be considered within the purview and scope of the claims appended hereto.

We claim:

1. An improved process for producing a substantially homogeneous population of plants of a predetermined hybrid variety of a crop which is capable of undergoing both self-pollination and cross-pollination comprising:
    (a) growing in a first planting area a substantially random population of (1) cytoplasmic male sterile plants which exhibit tolerance to at least one herbicide attributable solely to homozygous dominant nuclear genes, and (2) male fertile plants which are capable of pollinating said cytoplasmic male sterile plants and which lack said herbicide tolerance because the presence of homozygous recessive nuclear genes for such trait, whereby said cytoplasmic male sterile plants (1) and said male fertile plants (2) are pollinated with pollen derived from said male fertile plants and seed is formed on said cytoplasmic male sterile plants and on said male fertile plants,
    (b) harvesting in bulk said seed which is formed on said plants of said first planting area,
    (c) growing at least a portion of the seed from step (b) in a second planting area in the absence of segregation between the seed derived from said cytoplasmic male sterile plants which exhibit said herbicide tolerance attributable solely to homozygous dominant nuclear genes and said male fertile plants which lack said herbicide tolerance because of the presence of homozygous recessive nuclear genes for such trait, and
    (d) contacting prior to pollination substantially all of the plants present in said second planting area with a herbicide which is effective to destroy said plants resulting from seed formed on said male fertile plants of said first planting area, whereby a substantially homogeneous population of a predetermined hybrid variety is formed which resulted from seed formed on said male sterile plants of said first planting area.

2. An improved process for producing a substantially homogeneous population of plants of a predetermined hybrid variety of a crop according to claim 1 wherein said crop is selected from the group consisting of grain crops, forage crops, seed-propagated fruits, seed-propagated ornamentals, and industrial species.

3. An improved process for producing a substantially homogeneous population of plants of a predetermined hybrid variety of crop according to claim 1 wherein said crop is of the family Brassicaceae.

4. An improved process for producing a substantially homogeneous population of plants of a predetermined hybrid variety of crop according to claim 1 wherein said crop is of the genus Brassica.

5. An improved process for producing a substantially homogeneous population of plants of a predetermined hybrid variety of crop according to claim 1 wherein said crop is *Brassica napus*.

6. An improved process for producing a substantially homogeneous population of plants of a predetermined hybrid variety of crop according to claim 1 wherein said crop is *Brassica campestris*.

7. An improved process for producing a substantially homogeneous population of plants of a predetermined hybrid variety of crop according to claim 1 wherein said male fertile plants (2) are homozygous recessive maintainer plants for said cytoplasmic male sterile plants (1).

8. An improved process for producing a substantially homogeneous population of plants of a predetermined hybrid variety of a crop according to claim 1 wherein said male fertile plants (2) are homozygous dominant fertility restorer plants for said cytoplasmic male sterile plants (1).

9. An improved process for producing a substantially homogeneous population of plants of a predetermined hybrid variety of a crop according to claim 1 wherein said male fertile plants (2) are homozygous dominant fertility restorer plants for said cytoplasmic male sterile plants (1) and said resulting plants of step (d) are male fertile $F_1$ hybrid plants, and which includes the additional step of:

(e) harvesting seed which forms on said male fertile $F_1$ hybrid plants as a result of self-pollination.

10. An improved process for producing a substantially homogeneous population of plants of a predetermined hybrid variety of a crop according to claim 1 wherein said male fertile plants (2) are homozygous recessive maintainer plants for said cytoplasmic male sterile plants (1) and said resulting plants of step (d) are cytoplasmic male sterile plants, and which includes the additional steps of:

(e) growing in pollinating proximity to the substantially homogeneous population plants of step (d) a substantially homogeneous population of homozygous dominant fertility restorer plants for said cytoplasmic male sterile plants whereby said cytoplasmic male sterile plants of step (d) are pollinated with pollen from said restorer plants and seed is formed thereon, and (f) harvesting seed from said cytoplasmic male sterile plants at the conclusion of step (e) which is capable of forming a predetermined male fertile $F_1$ hybrid variety in the substantial absence of seed from said population of restorer plants.

11. An improved process for producing a substantially homogeneous population of plants of a predetermined hybrid variety of crop according to claim 1 wherein said pollination takes place with the aid of pollen-carrying insects.

12. An improved process for producing a substantially homogeneous population of plants of a predetermined hybrid variety of crop according to claim 1 wherein said herbicide is selected from the group consisting of sulfonylureas, glycine derivatives, and imidazolinones.

13. An improved process for producing a substantially homogeneous population of plants of a predetermined hybrid variety of crop according to claim 1 wherein said herbicide is chlorsulfuron.

14. An improved process for producing a substantially homogeneous population of plants of a predetermined hybrid variety of crop according to claim 1 wherein said herbicide is glyphosate.

15. An improved process for producing a substantially homogeneous population of plants of a predetermined hybrid variety of a crop according to claim 1 wherein said herbicide is amitrole.

16. An improved process for producing a substantially homogeneous population of plants of a predetermined hybrid variety of a crop according to claim 1 wherein said herbicide is bentazon.

17. An improved process for producing seed capable of forming a predetermined hybrid variety of a crop which is capable of undergoing both self-pollination and cross-pollination comprising:

(a) growing in a planting area a substantially random population of (1) cytoplasmic male sterile plants which exhibit tolerance to at least one herbicide attributable solely to nuclear genes, and (2) male fertile plants which are capable of pollinating said cytoplasmic male sterile plants and which lack said herbicide tolerance because of the absence of the required nuclear genes for such trait, whereby said cytoplasmic male sterile plants (1) are pollinated with pollen derived from said male fertile plants (2), (b) contacting following said pollination substantially all of the plants present in said planting area with a herbicide which is effective to destroy said male fertile plants and which is ineffective to destroy said cytoplasmic male sterile plants because of said herbicide tolerance attributable solely to said nuclear genes, and (c) harvesting seed from said cytoplasmic male sterile plants which is capable of forming said hybrid plants in the substantial absence of seed from said male fertile plants which initially grew in said planting area.

18. An improved process for producing seed capable of forming a predetermined hybrid variety of a crop according to claim 17 wherein said crop is selected from the group consisting of grain crops, forage crops, seed-propagated fruits, seed-propagated ornamentals, and industrial species.

19. An improved process for producing seed capable of forming a predetermined hybrid variety of a crop according to claim 17 wherein said crop is of the family Brassicaceae.

20. An improved process for producing seed capable of forming a predetermined hybrid variety of a crop according to claim 17 wherein said crop is of the genus Brassica.

21. An improved process for producing seed capable of forming a predetermined hybrid variety of a crop according to claim 17 wherein said crop is *Brassica napus*.

22. An improved process for producing seed capable of forming a predetermined hybrid variety of a crop according to claim 17 wherein said crop is *Brassica campestris*.

23. An improved process for producing seed capable of forming a predetermined hybrid variety of a crop according to claim 17 wherein said male fertile plants (2) are homozygous recessive maintainer plants for said cytoplasmic male sterile plants (1).

24. An improved process for producing seed capable of forming a predetermined hybrid variety of a crop according to claim 17 wherein said male fertile plants (2) are homozygous dominant fertility restorer plants for said cytoplasmic male sterile plants (1).

25. An improved process for producing seed capable of forming a predetermined variety of hybrid crop according to claim 17 wherein said cytoplasmic male sterile plants (1) possess homozygous dominant nuclear genes for said herbicide tolerance, and said male fertile plants (2) possess homozygous recessive nuclear genes for said herbicide tolerance, and the seed harvested in step (c) additionally is capable of forming hybrid plants which exhibit said herbicide tolerance.

26. An improved process for producing seed capable of forming a predetermined variety of hybrid crop according to claim 17 wherein said cytoplasmic male sterile plants (1) possess homozygous recessive nuclear genes for said herbicide tolerance, and said male fertile plants (2) possess homozygous dominant nuclear genes for said herbicide tolerance, and the seed harvested in step (c) is capable of forming hybrid plants which lack said herbicide tolerance.

27. An improved process for producing seed capable of forming a predetermined hybrid variety of crop according to claim 17 wherein said male fertile plants (2) are homozygous recessive maintainer plants for said cytoplasmic male sterile plants (1) and wherein said process includes the additional steps of:
    (d) growing as a substantially uniform population at least a portion of said seed from step (c) which is capable of forming plants which are cytoplasmic male sterile plants in pollinating proximity to a substantially uniform population of plants which are a homozygous dominant fertility restorer for said cytoplasmic male sterile plants whereby said cytoplasmic male sterile plants are pollinated with pollen derived from said restorer plants and seed is formed thereon, and
    (e) harvesting seed from said cytoplasmic male plants at the conclusion of step (d) which is capable of forming a predetermined male fertile $F_1$ hybrid variety in the substantial absence of seed from said population of restorer plants.

28. An improved process for producing seed capable of forming a predetermined hybrid variety of a crop according to claim 17 wherein said cytoplasmic male sterile plants (1) of step (a) possess homozygous dominant nuclear genes for said herbicide tolerance, and said male fertile plants (2) of step (a) are homozygous recessive maintainer plants for said cytoplasmic male sterile plants (1) and possess homozygous recessive nuclear genes for said herbicide tolerance, and wherein said process includes the additional steps of:
    (d) growing in a second planting area as a substantially random population at least a portion of the seed from step (c) which is capable of forming plants which are cytoplasmic male sterile and exhibit herbicide tolerance attributable solely to nuclear genes, and plants which are a homozygous dominant fertility restorer for said cytoplasmic male sterile plants and which lack herbicide tolerance because of the presence of homozygous recessive genes for such trait whereby said cytoplasmic male sterile plants are pollinated with pollen derived from said restorer plants,
    (e) contacting following said pollination substantially all of the plants present in said second planting area with a herbicide which is effective to destroy said restorer plants because of the lack of said herbicide tolerance and which is ineffective to destroy said cytoplasmic male sterile plants because of the presence of said herbicide tolerance, and
    (f) harvesting seed from said cytoplasmic male sterile plants of said second planting area which is capable of forming said hybrid plants in the substantial absence of seed from said restorer plants which initially grew in said second planting area.

29. An improved process for producing seed capable of forming a predetermined hybrid variety of crop according to claim 17 wherein said pollination takes place with the aid of pollen-carrying insects.

30. An improved process for producing seed capable of forming a predetermined hybrid variety of crop according to claim 17 wherein said herbicide is selected from the group consisting of sulfonylureas, glycine derivatives, and imidazolinones.

31. An improved process for producing seed capable of forming a predetermined hybrid variety of crop according to claim 17 wherein said herbicide is chlorsulfuron.

32. An improved process for producing seed capable of forming a predetermined hybrid variety of crop according to claim 17 wherein said herbicide is glyphosate.

33. An improved process for producing seed capable of forming a predetermined hybrid variety of crop according to claim 17 wherein said herbicide is amitrole.

34. An improved process for producing seed capable of forming a predetermined hybrid variety of a crop to claim 17 wherein said herbicide is bentazon.

35. An improved process for producing a substantially homogeneous population of plants of a predetermined hybrid variety of a crop which is capable of undergoing both self-pollination and cross-pollination comprising:
    (a) growing in a first planting area a substantially random population of (1) cytoplasmic male sterile plants which exhibit tolerance to a first at least one herbicide which is attributable solely to homozygous nuclear genes and exhibit tolerance to a second at least one herbicide which is attributable solely to different homozygous nuclear genes, and (2) male fertile plants which are homozygous recessive maintainer plants for said cytoplasmic male sterile plants and which lack said herbicide tolerance to said first at least one herbicide because of the absence of the required nuclear genes for such trait and exhibit tolerance to said second at least one herbicide attributable solely to said homozygous nuclear genes, whereby said cytoplasmic male sterile plants (1) and said maintainer plants are pollinated with pollen derived from said maintainer plants and seed is formed on said cytoplasmic male sterile plants and on said maintainer plants,
    (b) harvesting in bulk said seed which is formed on said plants of said first planting area,
    (c) growing in a second planting area a substantially random population of plants derived from seed harvested in step (b) together with homozygous dominant fertility restorer plants for said cytoplasmic male sterile plants which exhibit herbicide tolerance to said first at least one herbicide attributable solely to said homozygous nuclear genes and lack tolerance to said second at least one herbicide because of the absence of the required nuclear genes for such trait, (d) contacting prior to pollination substantially all of the plants present in said second planting area with said first herbicide which is effective to destroy said plants resulting from seed formed on said maintainer plants in step (a) whereby cytoplasmic male sterile plants and restorer plants remain, (e) pollinating said cytoplasmic male sterile plants and said restorer plants of step (d) with pollen derived from said restorer plants and seed is formed on said cytoplasmic male sterile plants and on said restorer plants, (f) harvesting in bulk the seed which is formed on said plants remaining in said second planting area, (g) growing in a third planting area a substantially random population of plants derived from seed harvested in step (f), and (h) contacting substantially all of the plants present in said third planting area with said second herbicide which is effective to destroy said plants resulting from the seed formed on said restorer plants of step (e), whereby a substantially homogeneous population of male fertile $F_1$ hybrid plants of a predetermined variety is formed.

36. An improved process for producing a substantially homogeneous population of plants of a predetermined hybrid variety of a crop according to claim 35 wherein said crop is selected from the group consisting of grain crops, forage crops, seed-propagated fruits, seed-propagated ornamentals, and industrial species.

37. An improved process for producing a substantially homogeneous population of plants of a predetermined hybrid variety of crop according to claim 35 wherein said crop is of the family Brassicaceae.

38. An improved process for producing a substantially homogeneous population of plants of a predetermined hybrid variety of crop according to claim 35 wherein said crop is of the genus Brassica.

39. An improved process for producing a substantially homogeneous population of plants of a predetermined hybrid variety of crop according to claim 35 wherein said crop is *Brassica napus.*

40. An improved process for producing a substantially homogeneous population of plants of a predetermined hybrid variety of crop according to claim 35 wherein said crop is *Brassica campestris.*

41. An improved process for forming a substantially homogeneous population of plants of a predetermined hybrid variety of a crop according to claim 35 whrein prior to step (a) the following process steps additionally are practiced:

(i) growing in a preliminary planting area a substantially uniform population of said cytoplasmic male sterile plants in pollinating proximity to a substantially uniform population of different maintainer plants which exhibit tolerance to said first at least one herbicide which is attributable solely to said homozygous nuclear genes and exhibit tolerance to said second at least one herbicide which is attributable solely to said different homozygous nuclear genes whereby said cytoplasmic male sterile plants are pollinated with pollen derived from said different maintainer plants and seed is formed thereon, and (ii) harvesting seed from said cytoplasmic male sterile plants which subsequently is grown in said first planting area of step (a).

42. An improved process for forming a subtantially homogeneous population of plants of a predetermined hybrid variety of a crop according to claim 35 whrein all of said homozygous nuclear genes for herbicide tolerance are homozygous dominant nuclear genes and said $F_1$ hybrid plants remaining in step (h) possess herbicide tolerance to said first and said second herbicides.

43. An improved process for forming a substantially homogeneous populaton of plants of a predetermined hybrid variety of crop according to claim 35 which includes the additional step of (i) harvesting seed which forms on said male fertile $F_1$ hybrid plants as a result of self-pollination.

44. An improved process for forming a substantially homogeneous populaton of plants of a predetermined hybrid variety of crop according to claim 35 wherein said pollination takes place with the aid of pollen-carrying insects.

45. An improved process for forming a substantially homogeneous population of plants of a predetermined variety of a crop according to claim 35 wherein at least one of said first and said second herbicides is selected from the group consisting of sulfonylureas, glycine derivatives, and imidazolinones.

46. An improved process for forming a substantially homogeneous population of plants of a predetermined hybrid variety of crop according to claim 35 wherein either said first or said second herbicide is chlorosulforon.

47. An improved process for forming a substantially homogeneous population of plants of a predetermined hybrid variety of crop according to claim 35 wherein either said first or said second herbicide is glyphosate.

48. An improved process for forming a substantially homogeneous population of plants of a predetermined hybrid variety of crop according to claim 35 wherein either said first or said second herbicide is amitrole.

49. An improved process for forming a substantially homogeneous population of plants of a predetermined hybrid variety of crop according to claim 35 wherein either said first or said second herbicide is bentazon.

50. An improved process for producing seed capable of forming a predetermined hybrid variety of a crop which is capable of undergoing both self-pollination and cross-pollination comprising:

(a) growing in a planting area a substantially random population of (1) cytoplasmic male sterile plants which exhibit tolerance to a first at least one herbicide which is attributable solely to homozygous nuclear genes, and exhibit tolerance to a second at least one herbicide which is attributable solely to different homozygous nuclear genes, and (2) male fertile plants which are homozygous recessive maintainer plants for said cytoplasmic male sterile plants and which lack said herbicide tolerance to said first at least one herbicide because of the absence of the required nuclear genes for such trait and exhibit tolerance to said second at least one herbicide attributable solely to said homozygous nuclear genes, whereby said cytoplasmic male sterile plants (1) and said maintainer plants are pollinated with pollen derived from said maintainer plants and seed is formed on said cytoplasmic male sterile plants and on said maintainer plants, (b) harvesting in bulk the seed which is formed on said plants of said first planting area, (c) growing in a second planting area a substantially random population of plants derived from seed harvested in step (b) together with homozygous dominant fertility restorer plants for said cytoplasmic male sterile plants which exhibit herbicide tolerance to said first at least one herbicide attributable solely to said homozygous nuclear genes and lack tolerance to said second at least one herbicide because of the absence of the required nuclear genes for such trait, (d) contacting prior to pollination substantially all of the plants present in said second planting area with said first herbicide which is effective to destroy the plants resulting from seed formed on said maintainer plants in step (a) whereby cytoplasmic male sterile plants and restorer plants remain, (e) pollinating said cytoplasmic male sterile plants and said restorer plants of step (d) with pollen derived from said restorer plants, (f) subsequently contacting substantially all of the remaining plants present in said second planting area with said second herbicide which is effective to destroy said restorer plants and which is ineffective to destroy cytoplasmic male sterile plants because of said herbicide tolerance attributable solely to said homozygous nuclear genes, and (g) harvesting seed from said cytoplasmic male sterile plants which is capable of forming $F_1$ hybrid plants in the substantial absence of seed form said maintainer and restorer plants which initially grew in said seconod planting area.

51. An improved process for producing seed capable of forming a predetermined hybrid variety of a crop according to claim 50 wherein said crop is selected from the group consisting of grain crops, forage crops, seed-propagated fruits, seed-propagated ornamentals, and industrial species.

52. An improved process for producing seed capable of forming a predetermined hybrid variety of crop according to claim 50 wherein said crop is of the family Brassicaceae.

53. An improved process for producing seed capable of forming a predetermined hybrid variety of crop according to claim 50 wherein said crop is of the genus Brassica.

54. An improved process for producing seed capable of forming a predetermined hybrid variety of crop according to claim 50 wherein said crop is of the genus Brassica napus.

55. An improved process for producing seed capable of forming a predetermined hybrid variety of crop according to claim 50 wherein said crop is of the genus Brassica campestris.

56. An improved process for producing seed capable of forming a predetermined hybrid variety of a crop according to claim 50 wherein prior to step (a) the following process steps additionally are practiced:

(i) growing in a preliminary planting area a subtantially uniform population of said cytoplasmic male sterile plants in pollinating proximity to a substantially uniform population of different maintainer plants which exhibit tolerance to said first at least one herbicide which is attributable solely to said homozygous nuclear genes and exhibit tolerance to said second at least one herbicide which is attributable solely to said different homozygous nuclear genes whereby said cytoplasmic male sterile plants are pollinated with pollen derived from said different maintainer plants and seed is formed thereon, and (ii) harvesting seed from said cytoplasmic male sterile plants which subsequently is grown in said first planting area of step (a).

57. An improved process for producing seed capable of forming a predetermined hybrid variety of a crop according to claim 50 wherein all of said homozygous nuclear genes for herbicide tolerance are homozygous dominant nuclear genes and the seed which is harvested in step (g) is capable of forming $F_1$ hybrid plants which possess herbicide tolerance to said first and said second herbicides.

58. An improved process for producing seed capable of forming a predetermined hybrid variety of crop according to claim 50 wherein said pollination takes place with the aid of pollen-carrying insects.

59. An improved process for producing seed capable of forming a predetermined variety of crop according to claim 50 wherein at least one of said first and said second herbicides is selected from the group consisting of sulfonylureas, glycine derivatives, and imidazolinones.

60. An improved process for prcducing seed capable of forming a predetermined hybrid variety of crop according to claim 50 wherein either said first or said secord herbicide is chlorosulfuron.

61. An improved process for producing seed capable of forming a predetermined hybrid variety of crop according to claim 50 wherein either said first or said second herbicide is glyphosate.

62. An improved process for producing seed capable of forming a predetermined hybrid variety of crop according to claim 50 wherein either said first or said second herbicide is amitrole.

63. An improved process for producing seed capable of forming a predetermined hybrid variety of crop according to claim 50 wherein either said first or said second herbicide is bentazon.

64. A *Brassica napus* seed product consisting of a substantially homogeneous assemblage of seeds which upon growth yield rape plants which exhibit a combination of cytoplasmic male sterility and tolerance to at least one herbicide attributable solely to homozygous dominant nuclear genes.

65. A *Brassica napus* seed product consisting of a substantially homogeneous assemblage of seeds which upon growth yield rape plants which exhibit a combination of cytoplasmic male sterility and tolerance to at least one herbicide attributable solely to homozygous recessive nuclear genes.

66. A *Brassica napus* seed product consisting of a substantially homogeneous binary admixture of seeds which upon growth yields:

(1) a first rape plant component which exhibits cytoplasmic male sterility and tolerance to at least one herbicide which is attributable solely to homozygous dominant nuclear genes, and (2) a second rape plant component which is capable of pollinating said first rape plant component, is a homozygous recessive maintainer for said cytoplasmic male sterility of said first rape plant component, and which lacks said herbicide tolerance because of the presence of homozygous recessive nuclear genes for such trait.

67. A *Brassica napus* seed product consisting of a substantially homogeneous binary admixture of seeds which upon growth yields:
 (1) a first rape plant component which exhibits cytoplasmic male sterility and tolerance to at least one herbicide which is attributable solely to homozygous recessive nuclear genes, and
 (2) a second rape plant component which is capable of pollinating said first rape plant component, is a homozygous recessive maintainer for said cytoplasmic male sterility of the first rape plant component, and which lacks said herbicide tolerance because of the presence of homozygous dominant nuclear genes for such trait.

68. A *Brassica napus* seed product consisting of a substantially homogeneous binary admixture of seeds which upon growth yields:
 (1) a first rape plant component which exhibits cytoplasmic male sterility and tolerance to at least one herbicide which is attributable solely to homozygous dominant nuclear genes, and
 (2) a second rape plant component which is capable of pollinating said first rape plant component, is a homozygous dominant fertility restorer for said first rape plant component, and which lacks said herbicide tolerance because of the presence of homozygous recessive nuclear genes for such trait.

69. A *Brassica napus* seed product consisting of a substantially homogeneous binary admixture of seeds which upon growth yields:
 (1) a first rape plant component which exhibits cytoplasmic male sterility and tolerance to at least one herbicide which is attributable solely to homozygous recessive nuclear genes, and
 (2) a second rape plant component which is capable of pollinating said first rape plant component, is a homozygous dominant fertility restorer for said first rape plant component, and which lacks said herbicide tolerance because of the presence of homozygous dominant nuclear genes for such trait.

70. A *Brassica napus* seed product consisting of a substantially homogeneous assemblage of seeds which upon growth yields male fertile $F_1$ hybrid rape plants which possess tolerance to at least one herbicide attributable solely to nuclear genes.

* * * * *